US005275176A

United States Patent [19]

Chandler

[11] Patent Number: 5,275,176

[45] Date of Patent: Jan. 4, 1994

[54] STABILIZATION DEVICE AND METHOD FOR SHOULDER ARTHROSCOPY

[76] Inventor: Eugene J. Chandler, 5702 E. Camelback Rd., Phoenix, Ariz. 85018

[21] Appl. No.: 816,324

[22] Filed: Dec. 30, 1991

[51] Int. Cl.[5] .......................... A61G 15/00; A61F 5/00

[52] U.S. Cl. .................................... 128/845; 606/242; 606/244

[58] Field of Search .................. 128/870, 845; 297/14, 297/16, 115; 606/237, 238, 240, 241, 242, 243, 244, 245

[56] References Cited

U.S. PATENT DOCUMENTS

| | | | |
|---|---|---|---|
| 1,117,403 | 11/1914 | Kreitzer | 606/241 |
| 1,989,434 | 1/1935 | Thompson | 606/244 |
| 2,749,911 | 6/1956 | Griffin | 606/242 |
| 3,815,586 | 6/1974 | Kazik | 606/237 |
| 4,271,830 | 6/1981 | Moon | 606/243 |
| 4,300,249 | 11/1981 | Taylor | 606/241 |
| 4,354,485 | 10/1982 | Safadago | 606/242 |
| 4,688,557 | 8/1987 | Bradstreet | 606/241 |
| 4,860,733 | 8/1989 | Parker | 606/237 |
| 4,903,689 | 2/1990 | Lannertone | 606/243 |

OTHER PUBLICATIONS

"Anterior Portal Selection For Shoulder Arthroscopy", Matthews, et al., *Arthroscopy: The Journal of Arthroscopy and Related Surgery,* vol. 1, No. 1, 1985, pp. 33–39.

"Shoulder Arthroscopy: A Modified Approach", Gross, et al., *Arthroscopy: The Journal of Arthroscopy and Related Surgery,* vol. 1, No. 3, 1985, pp. 156–159.

"Measurement of Brachial Plexus Strain in Arthroscopy of the Shoulder", Klein, et al., *Arthroscopy: The Journal of Arthroscopy and Related Surgery,* vol. 3, No. 1, 1987, pp. 45–52.

"Arthroscopic Subacromial Decompression: Analysis of One- to Three-Year Results", Harvard Ellman, M.D., *Arthroscopy: The Journal of Arthroscopy and Related Surgery,* vol. 3, No. 3, 1987, pp. 173–181.

"Arthroscopic Subacromial Decompression: Results According to the Degree of Rotator Cuff Tear", Esch, et al., *Arthroscopy: The Journal of Arthroscopy and Related Surgery,* vol. 4, No. 4, 1988, pp. 241–249.

"The Use of Somatosensory Evoked Potentials for Detection of Neuropraxia During Shoulder Arthroscopy", Pitman, et al., *Arthroscopy: The Journal of Arthroscopy and Related Surgery,* vol. 4, No. 4, 1988, pp. 250–255.

"Shoulder Arthroscopy with the Patient in the Beach Chair Position", Skyhar, et al., *Arthroscopy: The Journal of Arthroscopy and Related Surgery,* vol. 4, No. 4, 1988, pp. 256–259.

"Interscalene Block and the Beach-Chair Position for Shoulder Arthroscopy", Galinat, et al., *Arthroscopy: The Journal of Arthroscopy and Related Surgery,* vol. 5, No. 2, 1989, p. 161.

"Arthroscopic Acromioplasty for Lesions of the Rotator Cuff", Gary M. Gartsman, M.D., *The Journal of Bone and Joint Surgery, Inc.,* vol. 72-A, No. 2, Feb. 1990, pp. 169–180.

"Arthroscopic Acromioplasty", Altchek, et al., *The Journal of Bone and Joint Surgery, Inc.,* vol. 72-A, No. 8, Sep. 1990, pp. 1198–1207.

"Complications of Shoulder Arthroscopy", Bigliani, et al., *Orthopaedic Review,* vol. XX, No. 9, Sep. 1991, pp. 743–751.

*Primary Examiner*—Michael A. Brown
*Attorney, Agent, or Firm*—Cahill, Sutton & Thomas

[57] ABSTRACT

A surgical operating table particularly adapted for shoulder arthroscopy includes a central seat support, a leg support, and a back support modified to include detachable modular shoulder cutouts to gain access to the posterior aspect of the shoulder. The leg support and back support are hingedly connected to the seat support for positioning the patient in a sitting posture by operating mechanical crank arms. The patient is first supported in a supine position, anesthetized, secured to the table, and the table is thereafter configured to a sitting position. One of the modular shoulder cutouts is then removed to provide access to the shoulder upon which arthroscopy is to be performed.

13 Claims, 2 Drawing Sheets

STABILIZATION DEVICE AND METHOD FOR SHOULDER ARTHROSCOPY

BACKGROUND OF THE INVENTION

1. Field of the Invention

The present invention relates generally to apparatus and methods for performing arthroscopic shoulder surgery, and more particularly to a surgical operating table and method for performing shoulder arthroscopy with a patient in a sitting position.

2. Description of the Prior Art

The use of shoulder arthroscopy as a therapeutic and diagnostic tool has dramatically increased over the past decade. Patient recovery time is much shorter when arthroscopy is used as compared with open surgery, and shoulder arthroscopy has become particularly popular for sports-related shoulder injuries. Unfortunately, progress in shoulder arthroscopy has been hampered because of difficulty in positioning and stabilizing the patient's shoulder, while still allowing full exposure to all aspects of the shoulder and free movement of the arm.

Shoulder arthroscopy is usually performed with the patient under general anesthesia, lying in the lateral decubitus position, with the arm in traction to distend the shoulder joint. Such positioning and the application of such traction are generally shown in Pitman, et al., "The Use of Somatosensory Evoked Potentials for Detection of Neuropraxia During Shoulder Arthroscopy", *Arthroscopy*, Vol 4, No. 4, 1988, pages 250-255, and in Klein, et al., "Measurement of Brachial Plexus Strain in Arthroscopy of the Shoulder", *Arthroscopy*, Vol. 3, No. 1, 1987, pages 45-52. The lateral decubitus position requires that the operating table be essentially flat and horizontal. The patient is rolled on one side with the affected shoulder being uppermost, with the patient's back essentially perpendicular to the table, and with the lower leg flexed at the thigh and knee to stabilize the pelvis. Although the lateral decubitus position provides good access to the shoulder including the posterior aspect, the traction apparatus interferes with manipulation of the arm. The traction force causes distortion of the capsular anatomy, compromising arthroscopic visualization and impeding surgical technique, especially capsuloplasty. Also, the traction usually has to be adjusted intraoperatively to visualize the subacromial space, a cumbersome task. Finally, mechanical arm traction can cause neurological compromise and complications.

Shoulder arthroscopy can be performed with the patient in the semirecumbent position. For example, in Skyhar, et al., "Shoulder Arthroscopy with the Patient in the Beach-Chair Position", *Arthroscopy*, Vol. 4, No. 4, 1988, pages 256-259, the authors report on the use of a so-called "beach-chair sitting position" for shoulder arthroscopy. This position uses gravity assist for distraction of the joint and allows for gentle precise manipulation of the joint. However, to gain adequate access to the posterior aspect of the joint, the patient's torso must be pulled over the edge of the table and then rotated upward and supported in this awkward position with various supports such as beanbags, sandbags, blanket rolls, arm boards, or other outriggers. This position is precarious at best, and during the course of the operative procedure, the patient usually derotates with resultant loss of posterior exposure of the shoulder. Furthermore, with the patient in this position, the acromion is inclined posteriorly resulting in upward angulation of the arthroscope especially when performing a bursascopy. This position allows escaping saline to run down the arthroscope, not only fogging the lenses of the arthroscope and television camera, but also draining onto the surgeon's legs and feet and onto the floor.

Accordingly, it is an object of the present invention to provide an apparatus and method for performing shoulder arthroscopy which positively positions the patient in a stable manner without the need for sandbags, beanbags, blanket rolls or the like, and without the interference of ropes, pulleys, or other mechanical arm traction devices.

It is another object of the present invention to provide such an apparatus and method which provide ready access to the posterior aspect of the shoulder, while permitting convenient manipulation of the patient's arm.

Still another object of the present invention is to provide such an apparatus and method which do not require that the patient be pulled or rolled over the edge of a surgical table in order to gain access to the affected shoulder.

A further object of the present invention is to provide such an apparatus and method which permit for conversion to an open surgical procedure without the necessity of changing patient position, and without the necessity for reprepping and draping of the patient.

A still further object of the present invention is to provide a surgical table particularly facilitating arthroscopic shoulder surgery while still permitting other types of surgery to be performed thereon.

Yet another object of the present invention is to provide such an apparatus and method wherein the positioning of the patient upon the surgical table is fast, simple, and performed mechanically rather than by direct manual manipulation of the patient.

Still another object of the present invention is to provide such an apparatus and method which facilitates anesthesia of the patient.

Another object of the present invention is to provide such an apparatus and method which place the patient's acromion in a near horizontal plane for allowing the arthroscope to remain in a horizontal position.

These and other objects of the present invention will become more apparent to those skilled in the art as the description of the present invention proceeds.

SUMMARY OF THE INVENTION

Briefly described, and in accordance with a preferred embodiment thereof, the present invention relates to a surgical operating table adapted to perform shoulder arthroscopy and including a seat support, a leg support, and a back support. The seat support extends generally horizontal for supporting the central torso of a patient. The leg support is hingedly connected to one end of the seat support for supporting the legs of the patient. The back support is hingedly connected to the opposing end of the seat support for supporting the back and head of the patient. A mechanism, such as a mechanical crank drive, is provided for rotating the leg support and back support relative to the seat support about their respective hinged connections for causing a patient to rotate to a sitting position from an initial supine position. The back support includes right and left shoulder support cutout portions for selectively supporting the right and left shoulders of the patient, respectively. The right and left shoulder cutout portions are each selectively removable from the back support after the patient has been stabilized upon the surgical operating table in order to expose the shoulder upon which arthroscopic surgery is to be performed.

The right and left shoulder cutout portions are of the same thickness and construction as the remainder of the back support, and essentially constitute removable modules of the back support. A releasable securing mechanism releasably secures each of the removable shoulder cut-out modules within the same plane as the remainder of the back support. Preferably, the headrest secured to the back support is of a width which does not interfere with the sliding movement of the left and right shoulder cutout portions past the headrest, as when one of the removable modules is being removed from or reinserted into the back support.

The present invention also relates to a method of performing shoulder arthroscopy including the steps of supporting the patient in a sitting position upon an operating table, securing the back of the patient flat against the back support of the operating table, removing one of the shoulder cutout portions from the back support to expose the affected shoulder for access by the surgeon, and performing the arthroscopic procedure. This method preferably includes the steps of first configuring the operating table in a flat, horizontal configuration, positioning the patient upon the operating table in a supine (i.e., face-up, horizontal) position, anesthetizing the patient, and thereafter raising the back support of the operating table and lowering the leg support of the table to bring the patient toward the sitting position.

The aforementioned method may include the step of restraining the head of the patient against the headrest, as by wrapping adhesive tape over the forehead of the patient and around the back of the headrest, before cranking the back support toward an elevated position, to help stabilize the patient. Any tendency of the patient to slide forward after being raised toward the sitting position can be minimized by inclining the seat support at an upward angle of approximately 10-20 degrees from the end hingedly connected to the back support to the end hingedly connected to the leg support. A footrest is preferably attached to the leg support to support and stabilize the patient's feet when the leg support is lowered. Elastic bandages may be wrapped around the patient's legs to prevent venous blood pooling in the legs after the patient is raised into the sitting position.

BRIEF DESCRIPTION OF THE DRAWINGS

FIG. 2A is a side view of the surgical operating table configured in a flat, horizontal configuration.

FIG. 2B is a side view of the surgical table shown in FIG. 2A with the footrest deployed, and with the leg support cranked downwardly toward a sitting position.

FIG. 2C is a further side view of the surgical operating table shown in FIG. 2B after the back support portion thereof is raised toward a vertical position for placing the patient in a sitting position.

FIG. 2D is a rear view of the back support of the surgical operating table prior to removal of the right shoulder cut-out support portion, and wherein the patient's body is shown in dashed outline.

FIG. 2E is a rear view of the back support of the surgical operating table following removal of the right cut-out shoulder support portion for better exposing the shoulder to access by a surgeon.

DETAILED DESCRIPTION OF THE PREFERRED EMBODIMENTS

Figure 1:
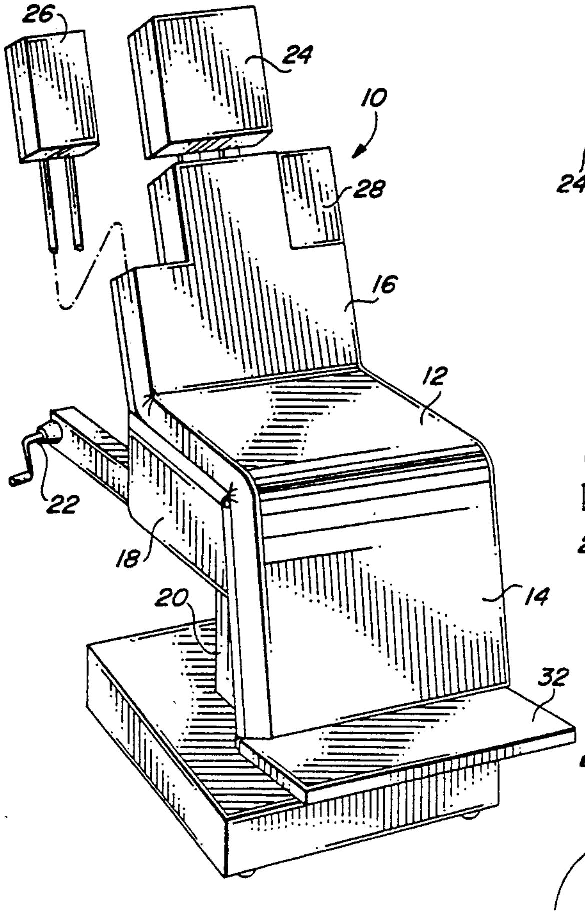
FIG. 1 is a perspective view of a surgical operating table constructed in accordance with the teachings of the present invention
Figure 2A:
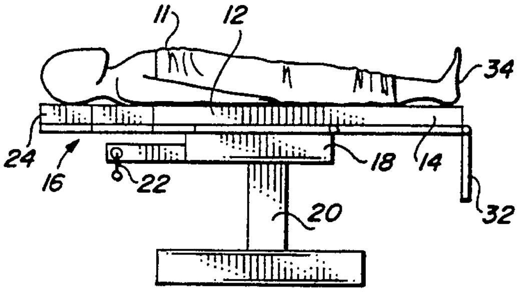
FIGS. 2A-2E illustrate the manner in which the surgical operating table shown in FIG. 1 may be used to facilitate shoulder arthroscopy.
Figure 2B:
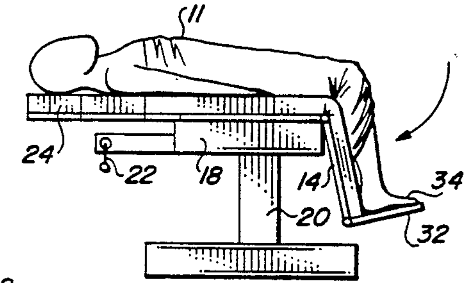
Figure 2C:
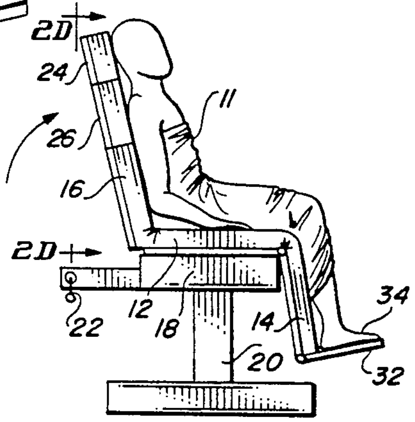

Within FIG. 1, a surgical operating table constructed in accordance with the teachings of the present invention is designated generally by reference numeral 10. Surgical operating table 10 includes a seat support 12, a leg support 14, and a back support 16, each provided with resilient padding. Referring briefly to FIG. 2C, seat support 12 supports the central torso of the patient 11, leg support 14 supports the legs of patient 11, and back support 16 supports the back and the head of patient 11. Leg support 14 is hingedly connected to a first end of seat support 12 for allowing leg support 14 to be rotated relative to seat support 12. Similarly, back support 16 is hingedly connected to an opposing second end of seat support 12 for allowing back support 16 to be rotated relative to seat support 12. Surgical operating tables generally operating in this manner are commercially available from Amsco of Erie, Pennsylvania.

As is conventional with most surgical operating tables, seat support 12 is supported upon a platform 18, which is in turn supported by a pedestal 20. Several crank drive mechanisms, such as that indicated by reference numeral 22, are provided within platform 18 for allowing a physician or nurse to selectively raise and lower leg support 14 and back support 16. In addition, while seat support 12 remains generally horizontal, a further crank drive mechanism (not shown) is also typically provided to adjust the angle of inclination of seat support 12. Referring briefly to FIGS. 2B and 2C, crank 22 may be rotated to cause back support 16 to rotate upwardly toward the sitting position shown in FIG. 2C. A similar mechanical crank is provided for lowering leg support 14, as shown by FIGS. 2A and 2B. Such manual cranks provide a mechanism for selectively rotating leg support 14 and back support 16 relative to seat support 12 about their respective hinged connections for supporting the patient in a sitting position, as indicated in FIG. 2C.

Still referring to FIG. 1, back support 16 includes a headrest 24 secured to the uppermost portion thereof. Typically, head rest 24 may be telescoped outwardly to accommodate taller patients. Headrest 24 may further be flexed forwardly or backwardly relative to back support 16 to position the patient's head and neck at various angles, if desired.

Figure 2E:
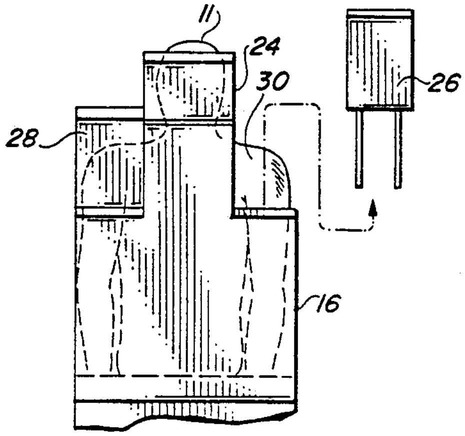
Figure 2D:
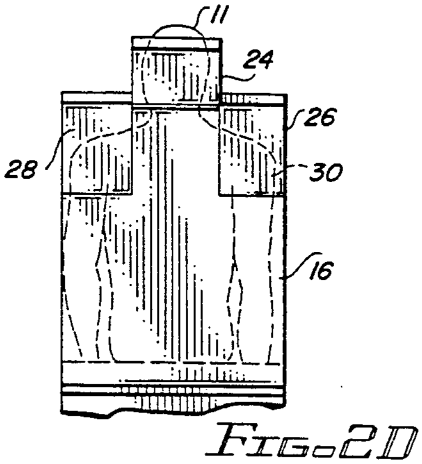

As shown in FIG. 1, back support 16 further includes removable right and left shoulder support cut-out portions 26 and 28 which, as shown in FIG. 2D, are adapted to support the right and left shoulders, respectively, of the patient. As further indicated in FIG. 1 and FIG. 2E, each of the right and left shoulder support portions 26 and 28 is releasably secured to back support 16. The right and left shoulder support portions 26 and 28 are selectively removable from back support 16 after the patient has been stabilized in a sitting position, as shown in FIG. 2C, to better expose the patient's shoulder 30 for arthroscopy.

With reference to FIGS. 1, 2A and 2B, leg support 14 also includes a footrest 32. As indicated in FIGS. 2B and 2C, footrest 32 is deployed to help support and stabilize the patient's feet 34 upon leg support 14.

Figure 3:
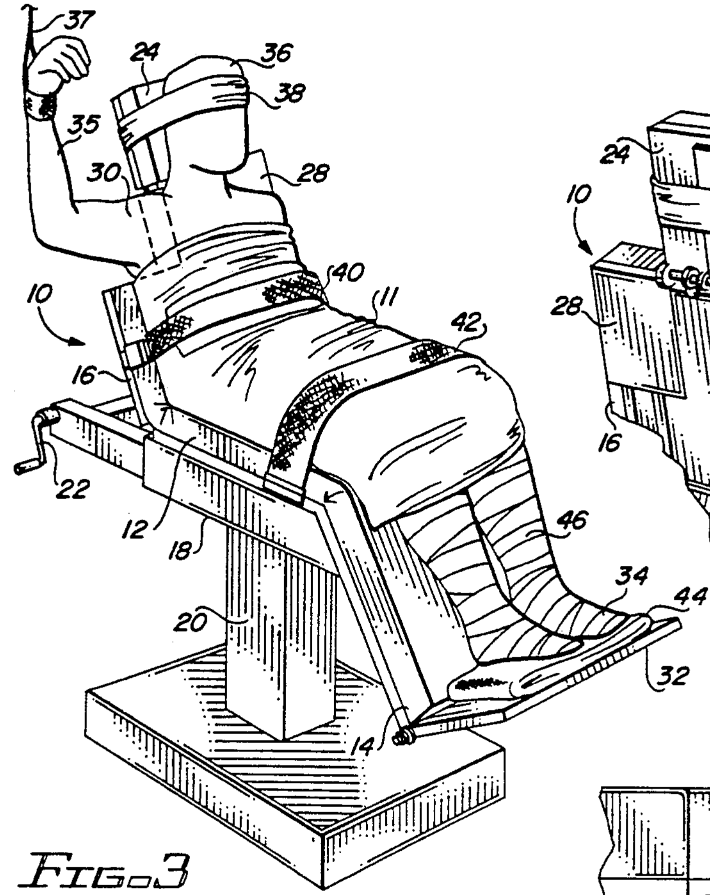
FIG. 3 is a perspective view of the surgical operating table shown in FIG. 1 with a patient secured upon the table and ready for arthroscopic surgery to the patient's right shoulder.
Figure 4:
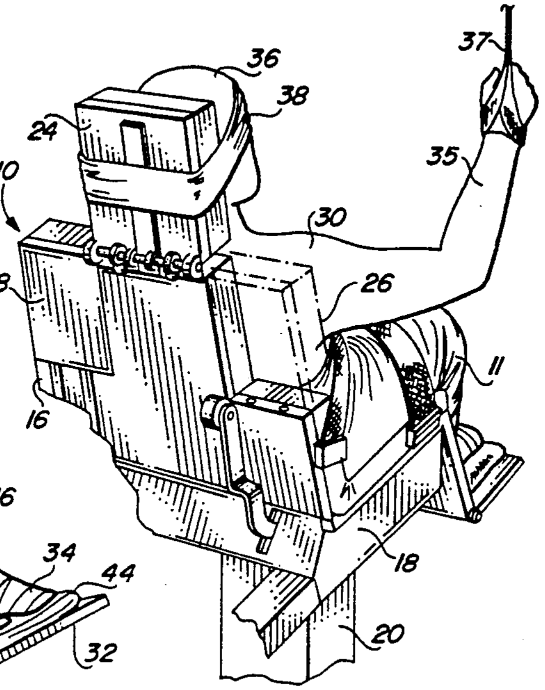
FIG. 4 is a rear perspective view of the patient and surgical operating table shown in FIG. 3, and wherein the removed right shoulder cut-out module is shown in dashed outline.

Referring to FIGS. 3 and 4, the patient 11 is shown in a sitting position upon surgical operating table 10 fully stabilized and ready for surgery. The patient's arm 35 is shown temporarily suspended by a wrist support 37; however, during surgery, arm 35 may be disengaged from wrist support 37 and freely moved by the physician and/or assistant to manipulate the shoulder 30 and/or to apply traction by gravity assist. The head 36 of the patient is restrained against headrest 24 by adhesive tape 38 wrapped about the forehead of the patient and secured behind headrest 24. Preferably, a thick foam rubber donut is positioned between the back of the patient's head and headrest 24 to further stabilize the head and to prevent any trauma to the head. Safety belts 40 and 42 are secured about the patient's chest and thighs to further stabilize the patient upon surgical operating table 10. The patient's feet 34 are supported by padding 44 and by footrest 32. As also shown within FIG. 3, the patient's legs 46 are wrapped with elastic bandages to diminish pooling of blood in the lower extremities during surgery.

Figure 6:
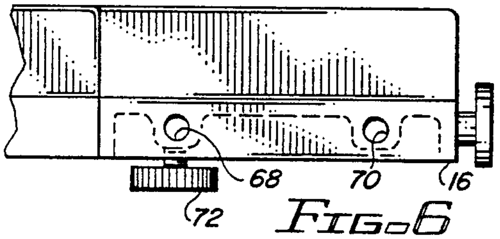
FIG. 6 is a partial top view of the back support taken along the lines designated 6—6, as shown in FIG. 5, and illustrating cylindrical sleeves into which corresponding support rods of the shoulder cut-out portion may be releasably secured.
Figure 5:
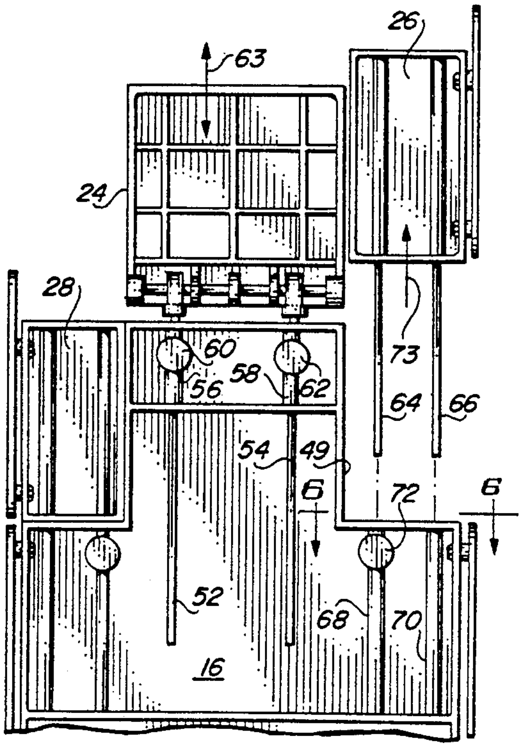
FIG. 5 is a rear view of the back support of the surgical operating table illustrating the manner in which the head rest and right and left shoulder cut-out support portions are releasably secured to the back support.
Figure 7:
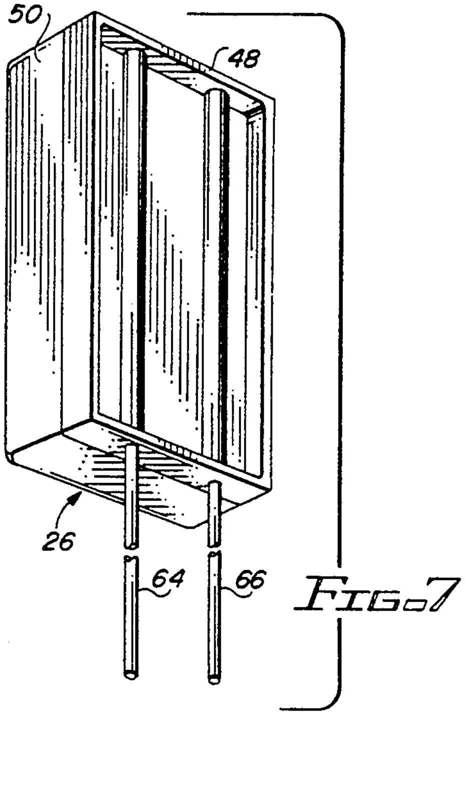
FIG. 7 is a rear perspective view of one of the shoulder cut-out modular portions.

FIGS. 5, 6, and 7 provide a better understanding of the manner by which removable shoulder cut-out modules 26 and 28 are releasably secured to back support 16. As shown in FIG. 7, the basic composition of removable shoulder cut-out portion 26 is identical to the construction of back support 16. A metal framework 48 provides a rigid foundation 49 adapted to be releasably coupled to a corresponding rigid foundation of back support 16. The front portion of metal framework 48 is covered by resilient padding 50, which matches the corresponding resilient padding secured over the front portion of back support 16. Preferably, the thickness of resilient padding 50 matches that of the corresponding resilient padding secured over back support 16, whereby the padded surface of right and left shoulder cut-out modules 26 and 28 lie in substantially the same plane as the padding covering back support 16 to form a smooth, continuous support surface.

Referring to FIG. 5, headrest 24 includes a pair of support rods 52 and 54 which telescope through sleeves 56 and 58, respectively, of back support 16. Tightening knobs 60 and 62 are threadingly engaged with sleeves 56 and 58, and are manipulated to tighten or loosen telescoping rods 52 and 54 within sleeves 56 and 58 to adjust the height of headrest 24, as indicated by arrow 63.

Similarly, shoulder cut-out module 26 includes a pair of telescoping support rods 64 and 66 extending downwardly therefrom. Support rods 64 and 66 are slidingly received within sleeves 68 and 70, respectively, of back support 16. A similar adjustment knob 72 may be manually tightened or loosened by the user to releasably lock shoulder cut-out module 26 to back support 16, or alternatively, to release shoulder cut-out module 26 therefrom, as indicated by arrow 73 in FIG. 5.

As indicated in FIG. 5, shoulder cut-out modules 26 and 28 are adapted to slide past headrest 24 when being removed from back support 16. Accordingly, headrest 24 may need to have a narrower profile than is ordinarily used for conventional surgical operating tables. Preferably, the width of headrest 24 plus the combined widths of shoulder cut-out modules 26 and 28 is made equal to the overall width of back support 16.

Those skilled in the art will understand that shoulder cut-out module 26 may be reinserted within back support 16 following shoulder arthroscopy by reinserting support rods 64 and 66 within sleeves 68 and 70, guiding shoulder cut-out module 26 downwardly past headrest 24 toward its initial fully-seated position, and retightening adjustment knob 72. With both shoulder cut-out modules restored to their initial position, surgical operating table 10 may be used for other conventional types of surgery as well. Thus, the modular design of should cut-out portions 26 and 28 preserves the original functions of surgical operating table 10 for general use.

It will be recalled that another aspect of the present invention relates to a method of performing shoulder arthroscopy. The preferred embodiment of such method will now be described. As shown in FIG. 2A, surgical operating table 10 is initially positioned in a substantially flat, horizontal configuration, with the back support 16 and leg support 14 portions lying substantially within the same horizontal plane as seat portion 12. The patient 11 is initially supported upon the operating table in a supine position as shown in FIG. 2A. The patient's head may then be restrained against headrest 24 in the manner shown and described above in reference to FIGS. 3 and 4. The patient's back is secured flat against the back support 16. The safety belts 40 and 42 shown in FIG. 3 are also secured. Preferably, the patient's legs are wrapped with elastic bandages in the manner described above, and footrest 32 and padding 44 are used to stabilize and secure the patient's feet upon leg support 14.

After stabilizing patient 11 upon surgical operating table 10 in the manner described above, general endotracheal anesthesia is induced by the anesthesiologist. Interscalene regional anesthesia can also be used. Back support 16 of surgical operating table 10 is gradually elevated to place the patient into the sitting position shown in FIGS. 3 and 4 so that the patient's acromion is almost horizontal. Simultaneously, seat support 12 is placed in 10°-20° of Trendelenburg position to prevent the patient from sliding forward. Leg support 14 is flexed 20°-30° to control rotation of the pelvis and the torso. Modular shoulder cutout 26 is then removed from back support 16 on the operative side. The patient's shoulder is prepped and the arm draped free. The boney landmarks are palpated and marked with ink. The glenohumeral joint is distended by injection of 20 cc. of 0.25% Bupivacaine with Epinephrine 1:200,000 solution as well as injection of the portal sites. The arthroscope is introduced through the posterior portal and an infusion cannula is inserted through an anterior portal. Diagnostic arthroscopy is performed under video control. Thereafter, arthroscopic surgery is performed upon the shoulder as indicated.

Conducting surgery with the patient in the sitting position offers a variety of advantages. General anesthesia in the sitting position may be more physiologic. Certainly ventilation of the lung bases is better because of improved chest expansion and better caudad motion of the diaphragm. Cardiovascular function is controversial because of the potential for circulatory instability, hypotension, and decreased cerebral perfusion. The patient must be monitored closely for hypotension and should it occur, the head must be lowered immediately and if necessary the patient can be placed in the Trendelenburg position. The legs are wrapped with elastic bandages to diminish pooling of blood in the lower extremities and the feet are lowered only enough to achieve rotation stability of the pelvis. Peripheral nerve complications are less in the sitting position, especially of the brachial plexus. Finally, the sitting position is more comfortable for the patient for local or regional anesthesia.

Identification of the boney landmarks is much easier in the sitting patient, even in the muscular or obese patient. The clavicle, acromion, coracoid, and the glenohumeral jointline are palpated and marked with ink for accurate portal placement. Portals used include posterior, anterior, superior, lateral, anterosuperior, and posteroinferior.

Shoulder arthroscopy with the patient in the sitting position eliminates the need for mechanical arm traction and the inherent neurological compromise caused by its use. Eliminating forceful traction also eliminates the distortion of the capsular anatomy; therefore, it is much easier to palpate the glenohumeral joint making the initial injection and distention of the joint much easier and more accurate. Once the joint is distended, it is much easier to insert the arthroscope with less risk of articular cartilage damage.

The sitting position allows for gravity assist in joint distraction and the arm draped free allows for easy and precise manipulation of the shoulder joint. Thus arthroscopic visualization of all parts of the joint is improved, and surgical instrumentation is much easier and more precise.

Another advantage of shoulder arthroscopy with the patient in the sitting position is that the surgeon has easy access to the anterior portals. Also the assistant is on the same side of the table as the surgeon; therefore, the assistant is in a better position to help the surgeon. Finally, conversion to an open surgical procedure can be done readily without the necessity of changing patient position or reprepping and draping.

The following arthroscopic surgical procedures may all be performed using the surgical operating table and method described above:

Repair of rotator cuff tears
Excision of calcific deposits of the rotator cuff
Capsuloplasty
Acromioplasty
Excision coracoacromial ligament
Excision of osteophytes of acromioclavicular joint
Bursectomy
Acromioclavicular joint arthroplasty
Chondroplasty (humerus/glenoid)
Abrasion arthroplasty (humerus/glenoid)
Excision of osteophytes (humerus/glenoid)
Excision tears of labrum
Loose body removal
Synovectomy Among the advantage of the shoulder arthroscopy table described above is that positioning of the patient is fast, easy, and done mechanically. The mechanical advantage cranks at the head of the table control all functions of elevating the back/head support, lowering the leg support, and tilting and inclining the seat support. The mechanical cranks can elevate the back support to 90°, lower the leg support to 90°, and adjust inclination and tilt of the seat support. The controls are smooth, swift, and efficient and can be made intraoperatively with ease and precision by the anesthesiologist or the nurse.

The gradual elevation of the back support of the table by the anesthesiologist during induction of anesthesia prevents hypotension. In the event that hypotension occurs intraoperatively, the anesthesiologist is in position to lower the back support of the table easily and quickly. Another advantage of the disclosed surgical operating table is that there is no need to turn or reposition the patient after induction of anesthesia. Also, there is no need for accessory supports such as sandbags, beanbags, blanket rolls, arm boards, or other outrigger apparatus. The mechanical cranks make it easy to adjust the patient position intraoperatively by either the anesthesiologist or other operating room personnel.

The disclosed surgical operating table provides excellent stability of the patient; therefore, an almost full upright sitting position can be achieved. This position places the acromion in a near horizontal plane allowing the arthroscope to remain in a horizontal position even when performing bursascopy, eliminating the problem of saline solution running down the arthroscope and fogging the lenses of the arthroscope and the television camera and draining onto the surgeon's feet and the floor. The full upright sitting position increases gravity-assist traction making manipulation of the arm easier, thereby improving arthroscopic visualization of the shoulder joint and making the surgical procedure more precise.

The surgical operating table disclosed herein allows for excellent stability of the patient's shoulder throughout the course of the procedure. With manipulation of the shoulder during the surgical procedure, the patient's position does not change; therefore, constant repositioning of the patient is avoided.

The design of the surgical operating table permits removal of either of the modular shoulder cutouts after anesthesia is induced. The removal of the cutout gives excellent exposure of the entire posterior aspect of the shoulder including the scapula. This access allows for easy manipulation of the arthroscope, thereby improving visualization of all parts of the joint and the subaoromial space.

Moreover, with the patient in the sitting position on the disclosed surgical operating table, it is easy to convert to an open surgical procedure without changing the patient's position (ie., when a large rotator cuff tear is encountered or when it is necessary to do a capsular shift to repair the capsule properly).

Finally, the modular design of the shoulder cutouts retains the original function of the standard surgical operating table for general use. Since the modular shoulder cutout back support is a permanent attachment to the table, no additional storage requirements are needed.

Those skilled in the art will appreciate that a surgical operating table has been described which greatly facilitates shoulder arthroscopy. It will also be appreciated that a method of performing shoulder arthroscopy has been described which offers unique advantages over known methods of performing shoulder arthroscopy. While the present invention has been described with respect to preferred embodiments thereof, the description is for illustrative purposes only and is not to be construed as limiting the scope of the invention. For example, while the removable shoulder cut-out modules described above are described as being releasably secured and/or removable, it is within the contemplation of the present invention to provide such cut-out modules as pivoting, hinged members which can be releasably pivoted downwardly out of the plane of the back support to provide access to the affected shoulder, and the term "releasably secured" should be construed to include this and other equivalent structures. Various other modifications and changes may be made by those skilled in the art without departing from the true spirit and scope of the invention as defined by the appended claims.

I claim:

1. A surgical operating table adapted to perform shoulder arthroscopy upon a patient, said surgical operating table comprising in combination:

a. a seat support having first and second opposing ends, said seat support supporting the central torso of the patient;

b. a leg support hingedly connected to the first end of said seat support for supporting the legs of the patient;

c. a back support hingedly connected to the second end of said seat support for supporting the back and head of the patient, said back support generally extending within a selected plane;

d. means for selectively rotating said leg support and back support relative to said seat support about said hinged connections for supporting the patient in a sitting position;

e. right and left shoulder support portions for supporting the right and left shoulder, respectively, of the patient, each of said right and left shoulder portions including securing means for securing the respective right and left shoulder support portions to said back support substantially in said selected plane, said securing means allowing one of said right and left shoulder support portions to be moved away from said selected plane of said back support and away from the shoulder of the patient independently of the other shoulder support portion after the patient has been stabilized in a sitting position to expose the right or left shoulder, respectively, of the patient for arthroscopy.

2. The surgical operating table recited by claim 1 wherein said back support includes a headrest, and wherein said right and left shoulder support portions extend proximate opposing sides of said headrest.

3. The surgical operating table recited by claim 2 wherein said back support has a first predetermined width, wherein each of said right and left shoulder support portions has a second predetermined width, and wherein said headrest has a third predetermined width, the third predetermined width being substantially equal to the first predetermined width less twice the second predetermined width.

4. The surgical operating table recited by claim 1 wherein said back support includes a rigid foundation covered by resilient padding, and wherein said right and left shoulder support portions also each include a rigid foundation covered by resilient padding.

5. The surgical operating table recited by claim 1 wherein said rotating means include mechanical cranks for elevating said back support and for lowering said leg support.

6. A method of performing arthroscopy upon a shoulder of a patient, the method comprising the steps of:

a. supporting the patient in a sitting position upon an operating table, the operating table including a back support for supporting the back and head of the patient;

b. securing the back of the patient flat against the back support of the operating table;

c. removing a portion of the back support of the operating table adjacent the shoulder upon which arthroscopic surgery is to be performed to better expose the posterior aspect of the shoulder for access by the surgeon; and d. performing arthroscopic surgery upon the exposed shoulder.

7. The method recited by claim 6 wherein the operating table further includes a leg support, said method including the further steps of:

a. Initially positioning the operating table in a substantially flat, horizontal configuration, with the back support and leg support lying substantially within the same horizontal plane;

b. Initially supporting the patient upon the operating table in a supine position;

c. anesthetizing the patient in said supine position; and d. thereafter raising the back support of the operating table and lowering the leg support of the operating table to support the patient in said sitting position.

8. The method recited by claim 7 wherein the back support includes a headrest, said method including the further step of restraining the head of the patient against the headrest.

9. The method recited by claim 8 wherein the patient's head is restrained against the headrest by wrapping adhesive tape over the forehead of the patient and securing the adhesive tape about the headrest of the back support.

10. The method recited by claim 7 wherein the operating table includes a seat support hingedly coupled at opposing ends to the back support and leg support, and wherein said method includes the step of inclining the seat support at an angle of 10 to 20 degrees from horizontal with the back support end of the seat support being lower than the leg support end of the seat support, to prevent the patient from sliding forward during surgery.

11. The method recited by claim 7 further including the step of attaching a footrest to the leg support to support the feet of the patient when the leg support is lowered toward the sitting position.

12. The method recited by claim 7 wherein the step of lowering the leg support includes the step of lowering the leg support to an angle of approximately 20 degrees or more from vertical.

13. The method recited by claim 7 further including the step of wrapping the patient's legs with elastic bandages before lowering the leg support to prevent venous blood pooling during surgery.

* * * * *